(12) United States Patent
Locke et al.

(10) Patent No.: US 7,770,855 B2
(45) Date of Patent: Aug. 10, 2010

(54) HANGING APPARATUS FOR FIXING A MEDICAL DEVICE TO A SUBSTANTIALLY HORIZONTAL OR SUBSTANTIALLY VERTICAL SUPPORT STRUCTURE

(75) Inventors: Christopher Brian Locke, Bournemouth (GB); Aidan Marcus Tout, Nomansland (GB)

(73) Assignee: KCI Licensing, Inc, San Antonio, TX (US)

( * ) Notice: Subject to any disclaimer, the term of this patent is extended or adjusted under 35 U.S.C. 154(b) by 467 days.

(21) Appl. No.: 11/903,209

(22) Filed: Sep. 19, 2007

(65) Prior Publication Data
US 2008/0077078 A1    Mar. 27, 2008

Related U.S. Application Data

(60) Provisional application No. 60/845,993, filed on Sep. 19, 2006.

(51) Int. Cl.
*G09F 7/18* (2006.01)
(52) U.S. Cl. .................................... 248/230.2; 248/214
(58) Field of Classification Search ................. 248/214, 248/220.21, 226.12, 228.2
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |

(Continued)

FOREIGN PATENT DOCUMENTS

AU        550575 A1      8/1982

(Continued)

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(Continued)

*Primary Examiner*—Amy J Sterling

(57) ABSTRACT

A hanging apparatus is provided that facilitates the attachment of a medical instrument to a support structure. The mechanism includes a generally longitudinal, telescoping assembly that extends outward from the back of the medical instrument and positions a rotatable arm to serve as one face of a clamp, opposing the back of the medical instrument as the second face of the clamp. The mechanism assembly includes a cylindrical shaft that extends outward against the tension force of a spring from a housing component of the assembly. A cam mechanism within the hanging apparatus allows for locking and tightening of the clamp against the support structure after closure of the clamp under the influence of the tensioning spring.

7 Claims, 3 Drawing Sheets

U.S. PATENT DOCUMENTS

| | | |
|---|---|---|
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,108,213 A | 4/1992 | Shields |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,378,826 B1 | 4/2002 | Knaub et al. |
| 6,471,197 B1 | 10/2002 | Denk et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,100,244 B2 | 9/2006 | Qin et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0226943 A1* | 12/2003 | Laisement et al. ....... 248/230.2 |
| 2006/0027979 A1 | 2/2006 | Yang et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundations," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

\* cited by examiner

HANGING APPARATUS FOR FIXING A MEDICAL DEVICE TO A SUBSTANTIALLY HORIZONTAL OR SUBSTANTIALLY VERTICAL SUPPORT STRUCTURE

CROSS-REFERENCE TO RELATED APPLICATIONS

This application claims the benefit of U.S. Provisional Application No. 60/845,993, filed Sep. 19, 2006, which is hereby incorporated by reference.

BACKGROUND OF THE INVENTION

1. Field of the Invention

The present invention relates generally to hanging mechanisms and in particular to a hanging apparatus for fixing a medical device to a support structure.

2. Description of Related Art

Patients within hospital and extended health care settings frequently must utilize medical instrumentation and other medical devices associated with the monitoring and/or treatment of a variety of conditions. Such instruments and devices that often must be positioned in close proximity to the patient, range from simple blood pressure and temperature monitoring devices to more complex gas and fluid pumps or reduced pressure treatment system devices. While some of these instruments are constructed and positioned on their own moveable carts or wheeled carriages, many more are sized and structured so as to require placement on a tabletop or on some other support fixture associated with the patient's location.

A common structure utilized to retain such medical instruments and devices is an IV pole, so named because of its primary purpose of hanging an intravenous (IV) solution bag or container for administration of fluids to the patient. IV poles are typically fitted with wheeled stands that allow the pole to be moved, especially with a patient that is ambulatory. This wheeled stand structure also permits the IV pole and the associated objects it supports to be moved in and out of the patient's locale as needed.

The use of IV poles is sufficiently prevalent that many medical instruments and devices have been structured with brackets and/or clamps that are sized and shaped to be fixed to the vertically oriented pole structure. These brackets and/or clamps sometimes take the form of clips or screw-tightened enclosures. The vertical orientation of these clamps, however, makes it difficult to use the same attachment structure on any object other than the vertically structured IV pole.

Other structures typically found in close proximity to patients requiring the use of medical instruments and devices are hospital type bed frames and patient wheelchairs. Each of these latter two structures will generally present horizontal bars, rails, or the like to which medical instruments and devices might be attached if they are so configured to receive and retain the horizontal bar structures. In general, however, the clamp or attachment structures associated with medical devices and instruments do not lend themselves to easy modification between a structure that is appropriate for attachment to a vertical pole and a structure appropriate for attachment to a horizontal bar.

It would be desirable to have a clamping or attachment device capable of easy structural modification such that the same device could serve to attach a medical instrument or medical device to a vertically oriented stand, such as an IV pole, or to a horizontally oriented stand, such as a hospital bed railing or a bar associated with a wheelchair. It would be desirable if the attachment mechanism could be easily switched between an orientation appropriate for horizontal attachment and an orientation appropriate for vertical attachment. It would be desirable if this versatility in attachment orientation was accompanied by a secure closure in either orientation, such that the medical instrument or medical device was unlikely to become dislodged from the support structure.

It would further be beneficial if, in the use of the clamp or attachment mechanism, a definitive indication of the secure state of the clamp could be provided.

BRIEF SUMMARY OF THE INVENTION

In fulfillment of the above and other objectives, one embodiment of the present invention provides a clamping mechanism that facilitates the attachment of a medical instrument or device to an IV pole, a bed, or a wheelchair structure. The mechanism incorporates components that allow its use in conjunction with either a vertically oriented support structure (such as an IV pole) or a horizontally oriented support structure (such as a bed rail or a wheelchair rail). The mechanism includes a generally longitudinal, telescoping assembly that extends outward from the back of the medical instrument and positions a rotatable arm to serve as a clamp opposing the back of the medical instrument or device. The mechanism assembly includes a cylindrical shaft that extends outward (against the tension force of a spring) from a housing of the medical instrument. Cammed surfaces within internal rotating components of the clamping mechanism assembly allow for tightening of the clamp against the support structure after closure of the clamp under the influence of the tensioning spring. A knob allows the user to rotate the internal components of the assembly to further engage the cammed surfaces and tighten (close) the clamp against the support structure.

Other objects, features, and advantages of the present invention will become apparent with reference to the drawings and detailed description that follow.

DETAILED DESCRIPTION OF THE PREFERRED EMBODIMENT

Figure 1A:
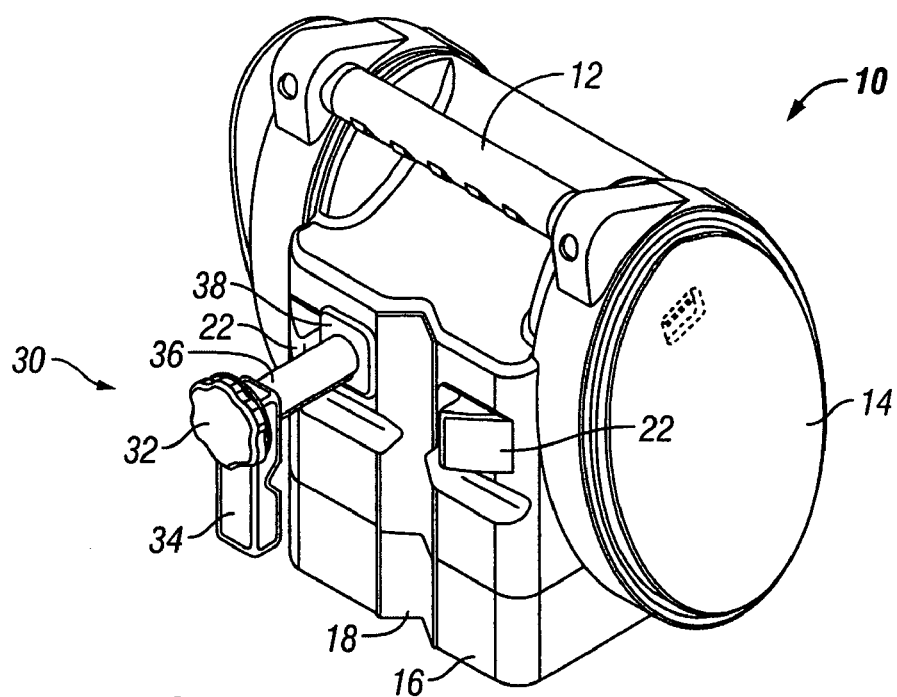
FIG. 1A is a perspective view of a medical instrument incorporating a hanging apparatus according to an embodiment of the present invention, the hanging apparatus being oriented in a vertical position for attachment to a horizontally-oriented support structure.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The hanging apparatus of the present invention may be easily manufactured as part of an original equipment structure for a medical instrument or a medical device that is to be positioned adjacent a patient requiring use of the instrument. The hanging apparatus may also, in certain circumstances, be retrofit into existing devices where space within the device enclosure allows such placement. In either case, the first step in utilizing the benefits of the assembly is to determine if the medical device or instrument must be attached to an IV pole, to a bed railing, or to a wheelchair frame component. In some instances, it may be possible to choose between the various support structures for the instrument, and to select that support platform most advantageous to the patient, or most unobtrusive to the patient's environment.

If an IV pole is to be utilized to support the medical instrument, then the hanger arm structure of the present invention is positioned in a substantially horizontal position so as to engage the vertical orientation of the IV pole. If the instrument is to be positioned on a bed or a wheelchair, the arm of the hanger may be positioned in a substantially vertical orientation by rotating the arm downward from the horizontal orientation approximately 90 degrees. After rotation, the clamping mechanism assembly is pulled outward from the back of the medical instrument by gripping a knob positioned on the end of the assembly. The mechanism is then pulled out in telescoping fashion against the force of an internal spring, and the arm is placed around the pole (in the case of an IV pole) or over the railing of the bed or frame of the wheelchair (in the case of a horizontal support structure). The user then gradually releases the mechanism under the spring tension by allowing the assembly to return towards the back of the instrument to the point where the arm and the back of the instrument each come into contact with the pole or railing. This spring tension is sufficient to close the arm against the horizontal or vertical support structure but is not sufficient to retain the instrument tightly against the support structure as gravity acts on the instrument.

In order to tightly secure the clamp around the support structure, the knob is turned clockwise until an arrow indicator on the device (on the back face of the instrument) lines up with a "locked" symbol on the knob, or an audible click is heard representing the position of the assembly in a detent associated with this stepwise rotation. The mechanism is thereby positioned in a locked condition. To further increase the force of the clamp against the longitudinal support structure, the knob may be further turned clockwise in a manner that, due to the internal configuration of the assembly described in more detail below, draws the clamp arm further in towards the back face of the instrument and thereby increases the clamping force against the support structure.

To remove the clamping mechanism assembly (and the medical instrument), the process is generally reversed. The knob is turned counterclockwise until the arrow indicator on the instrument lines up with an "socked" symbol on the knob. Once again, the mechanism may then be pulled outward from the back of the medical instrument or device, again under spring tension, to the point where the support structure (vertical or horizontal) is released from the clamping enclosure. The medical instrument may then be removed from the support structure for repositioning or removal from the patient environment. The detailed manner in which the hanging apparatus of the present invention operates to achieve the above functionality is now described in detail.

Figure 1B:
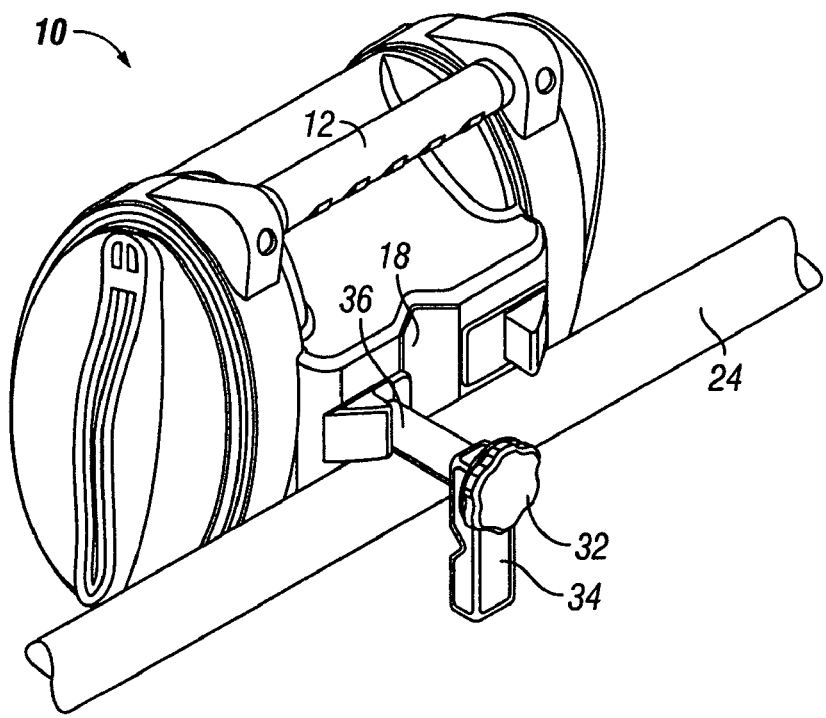
FIG. 1B is a perspective view of the medical instrument of FIG. 1A affixed to the horizontally-oriented support structure.

Reference is made to FIGS. 1A, 1B, 2A, and 2B for a brief description of the primary external components of a hanging apparatus 30 according to an embodiment of the present invention and the manner in which the hanging apparatus is associated with a medical instrument or a medical device. In the example shown in FIG. 1A, a reduced pressure treatment pump 10 is sized and structured to be appropriate for placement in close proximity to a patient undergoing, for example, reduced pressure tissue treatment. Instrument 10 in this case includes a handle 12 for portability positioned on the top of instrument housing 14. Of particular importance to the use and application of the present invention is the structure of the back panel 16 of instrument 10, which structure is described in more detail below. Also disclosed in FIG. 1 are the primary external components associated with hanging apparatus 30. In this view shown in FIG. 1A, a knob 32, a clamp arm 34, a clamp shaft 36, and a clamp housing 38 are each disclosed. It should be noted that the orientation of clamp arm 34 shown in FIGS. 1A and 1B is suitable for positioning medical instrument 10 on a horizontally oriented support structure 24.

The construction of medical instrument 10 shown in FIGS. 1A, 1B, 2A, and 2B is preferably designed to work in complimentary fashion with hanging apparatus 30. The back panel 16 of medical instrument 10 is structured to facilitate attachment to either a horizontal or vertical support structure. A vertical channel 18 is formed into back panel 16 of instrument 10 appropriate for receiving a vertically oriented support structure (as shown in more detail in FIG. 2B). Horizontal channel 20 is likewise configured to facilitate retention of a horizontally oriented support structure 24 as shown in FIG. 1B. Horizontal channel 20 is positioned on back panel 16 immediately below the placement of hanging apparatus 30 in such a manner that the simple positioning of instrument 10 over the horizontal support structure 24 lands the support structure into channel 20 and against the underside of hanging apparatus 30. Gravity inclines the placement of instrument 10 into this configuration.

Further facilitating the placement of instrument 10 over and in association with a horizontal support structure 24, are guide extensions 22. Positioned above channel 20 and substantially in-line with hanging apparatus 30, guide extensions 22 serve to further facilitate the placement of instrument 10 on top of and tightly against a horizontal support structure 24. When utilized in the vertical orientation, described below in conjunction with FIGS. 2A and 2B, one of the two guide extensions 22 continues to facilitate the positioning of instrument 10 on the vertically oriented support structure.

Figure 2A:
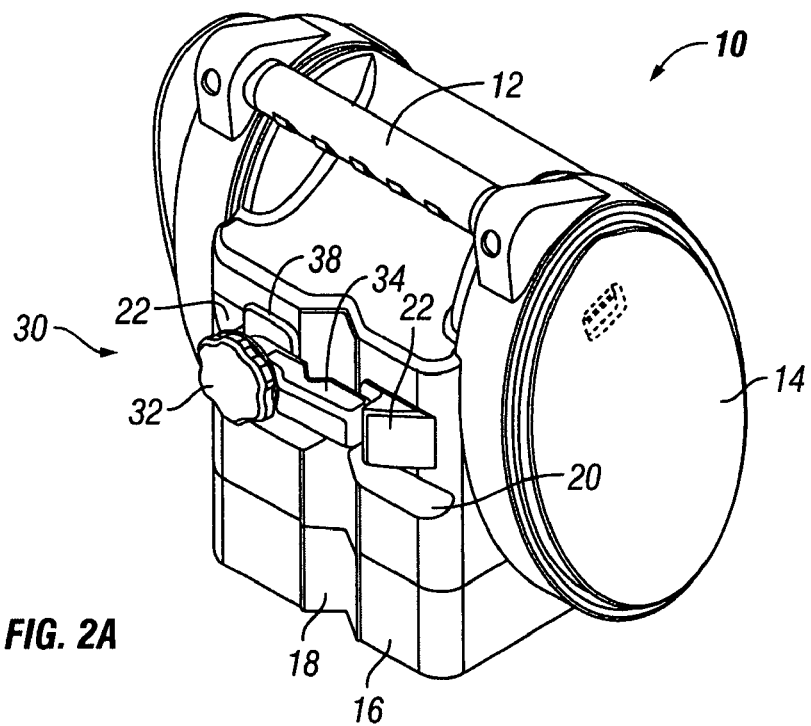
FIG. 2A is a perspective view of the medical instrument of FIG. 1A, the clamping incorporating the hanging apparatus being oriented in a horizontal position for attachment to a vertically-oriented support structure.
Figure 2B:
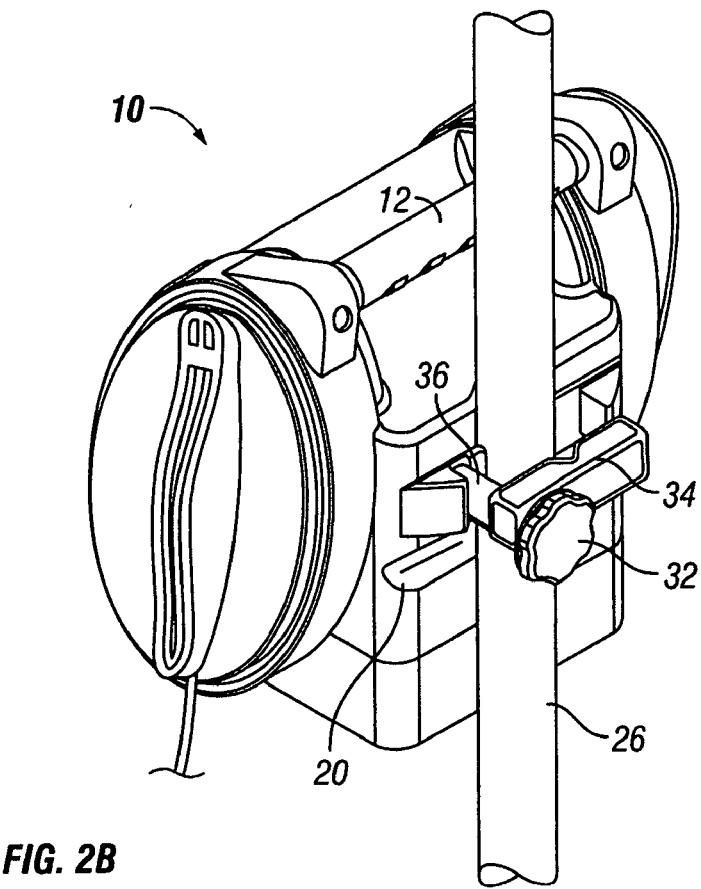
FIG. 2B is a perspective view of the medical instrument of FIG. 2A affixed to the vertically-oriented support structure.

FIGS. 2A and 2B, as mentioned above, illustrates hanging apparatus 30 with clamp arm 34 positioned in a substantially horizontal position suitable for facilitating the clamping attachment of instrument 10 to a vertical support structure 26 (shown in dashed outline). FIGS. 2A and 2B therefore represent the configuration appropriate for use in conjunction with an IV pole or the like. FIGS. 1A and 1B, on the other hand, disclose the configuration appropriate for use in conjunction with a bed rail or a wheelchair frame or the like.

In use, prior to placement on the support structure, clamp arm 34 is rotated into the appropriate configuration dependent upon the support structure orientation being utilized. By internal mechanisms that are described in more detail below, the spring tensioned features of the hanging apparatus 30, pull clamp arm 34 into contact with the support structure (whichever direction it is oriented) at which point the user rotates knob 32, preferably in a standard clockwise tightening direction, to further secure hanging apparatus 30 against the support structure component. It should be noted that the orientation of the various structures described above are such that in either case, a loose clamp does not result in a completely open clamp such that the instrument 10 might fully dislodge from the support structure. In the horizontal orientation shown in FIG. 1, a loose clamp would still retain the instrument 10 in close proximity to the horizontal support structure by the force of gravity downward on the instrument. Only after some loosening of the clamp, by telescoping movement outward as against the tension of the internal spring, would the instrument be removable from the horizontal support structure. Likewise, in conjunction with the vertical orientation shown in FIGS. 2A and 2B, the length of the clamp arm 34, and its position proximate to the guide extension 22, is such that mere loosening of the clamp does not create an opening sufficient alone for removal of the instrument from the clamp enclosure. While the components of hanging apparatus 30, again as described in more detail below, are such as to generally prevent the loosening of the clamp under normal use, these further structural features help prevent any significant dislodgement of the instrument from the chosen support structure.

Figure 3:
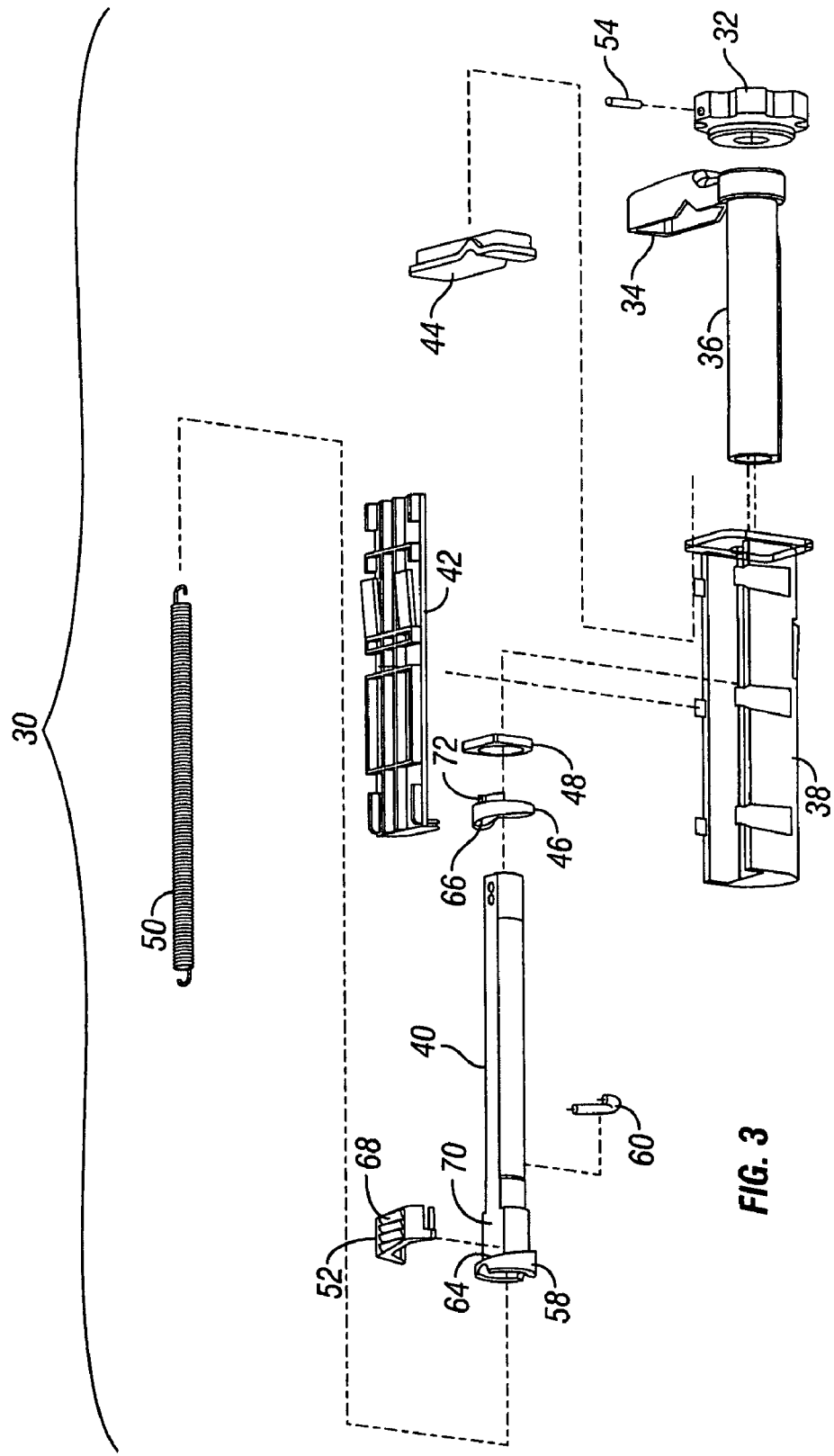
FIG. 3 is an exploded perspective view of the components of the hanging apparatus of FIG. 1A.

Reference is now made to FIG. 3 for a more detailed description of the various components of the hanging apparatus 30 shown generally in FIGS. 1 & 2. For reference, hanging apparatus 30, shown in FIG. 3, includes the external components described above, namely knob 32, clamp arm 34, and clamp shaft 36. Additionally, clamp housing 38 is fully disclosed in FIG. 3 wherein only the external face of clamp housing 38 is visible in FIGS. 1A, 1B, 2A, and 2B. As illustrated in FIG. 3, hanging apparatus 30 may be constructed wholly separate from the structure and components of instrument 10, and may in fact be later assembled into instrument 10, as long as appropriate accommodations are made within the instrument enclosure to receive and retain the assembly.

The components of hanging apparatus 30 are selected, structured, and positioned to accomplish three basic functions. The first function, in the process of securing the medical instrument to the support structure, is the ability to open and extend the clamp to receive the support structure for attachment. A second function is the free rotation of clamp arm 34 through at least a 90° movement so as to orient the arm for either vertical or horizontal attachment. To fulfill a third function, the components are structured to permit a tightening of the clamp, beyond the force of the tension spring, through the use of cammed surfaces that draw the clamp inward upon rotation of the knob of the clamp assembly. The components that achieve each of these functions are described in more detail below.

Clamp housing 38 is structured and sized to rotatably receive clamp shaft 36 to a point where clamp arm 34 comes into near contact with the outward face of clamp housing 38. Housing cover 42 provides both a means for closing clamp housing 38 (after the insertion of the balance of the assembly components) and, structured as shown in FIG. 3, a means for retaining the entire hanging apparatus 30 within the instrument enclosure utilizing the preferenced clips shown on the top of housing cover 42 and on the sides of housing 38.

The view in FIG. 3 shows further detail of the components associated with the external structures of hanging apparatus 30. These include a clamp face plate 44, configured to be positioned with and retained by clamp arm 34 as shown. A notch or channel in clamp face plate 44 is designed to receive and center the longitudinal pole or railing to which the device is to be clamped. This channel aligns with and opposes either of the two similar channels 18 and 20 described above in association with FIGS. 1A, 1B, 2A, and 2B. In this manner, a pole or bar of varying diameters may be accommodated within the structures of the clamp of the present invention. In the preferred embodiment, clamp face plate 44 may be constructed of a resilient elastomeric material or the like to facilitate clamp tightening.

Knob 32 is shown as it is positioned at one end of clamp shaft 36, placing clamp arm 34 between the knob 32 and the shaft 36. In the preferred embodiment, clamp arm 34 is rigidly fixed to and rotates with shaft 36. Set screw 54 is positioned within knob 32 to engage internal shaft 40 and fix knob 32 to the end thereof. This connection and its function are described in more detail below.

Reference is again made to FIG. 3 for a more detailed description of the internal components of the hanging apparatus 30 and the manner in which they operate to accomplish each of the functions described above. Internal shaft 40 is designed to move freely in a longitudinal direction out from clamp housing 38 under the influence of its attachment to knob 32 and its concentric positioning within tubular shaft 36. Set screw 54 passes through an aperture in knob 32 and engages an aligned aperture in a proximal end of internal shaft 40. Positioned inside of internal shaft 40 is tension spring 50, which is fixed at one end within internal shaft 40 by way of set screw 54. The opposing end of tension spring 50 is fixed relative to housing 38 and/or housing 14. In this manner, the assembly components that include knob 32, clamp arm 34, clamp shaft 36, and internal shaft 40 may be drawn out from clamp housing 38 in telescoping fashion, in opposition to the tension provided by tension spring 50, in a manner that opens the clamp to receive the support structure horizontal or vertical component. End plate 48, positioned within clamp housing 38, and through which internal shaft 40 extends, limits this longitudinal movement of the described components out from housing 38. End plate 48 further limits the rotational range of the internal shaft 40 due to its interaction with second cam member 46 described below. Limiting the rotational movement of the internal shaft 40 prevents the locking and tightening mechanisms of the hanging apparatus 30 from separating the housing cover 42 from the clamp housing 38.

In the manner of the assembled components described above, it can be seen that through the combination of hollow clamp shaft 36, attached to clamp arm 34, surrounding and rotatable about internal shaft 40, clamp arm 34 may be turned between a horizontal position (suitable for engagement with a vertically oriented support structure), and a vertical position (suitable for clamping onto a horizontal support structure). This motion therefore accomplishes the second of the three functions mentioned above, namely the ability to re-orient clamp arm 34 and its associated clamp face plate 44, for engagement of either a horizontal or a vertical oriented support structure.

Finally, a cam mechanism comprising first and second cam members, 58, 46, as well as a locking member 52, provide the third functionality described above, namely the ability to rotate the internal components of the assembly in such a manner as to further tighten the clamp against the support structure. First and second cam members 58, 46 include complementary inclined surfaces 64, 66 and are fixed relative to the internal shaft 40. The internal shaft 40 and the cam members 58, 46 will rotate under the influence of the user turned knob 32. The locking member 52 is rotatably affixed to the internal shaft 40 by an attachment spring 60. The locking member 52 is positioned on the internal shaft 40 between the inclined surfaces of the first and second cam members and includes a second plurality of teeth 68 configured to mate with a first plurality of teeth (not shown) along a bottom surface of the housing cover 42. When the housing cover 42 is fixed to the clamp housing 38, the first plurality of teeth are aligned with the longitudinal enclosure of the clamp housing 38. When the internal shaft 40 is in an unlocked position, the locking member 52 is positioned on a substantially flat surface 70 of the internal shaft 40. As the internal shaft 40 is rotated into a locked position, the locking member 52 moves off of the substantially flat surface 70, which causes a radially outward displacement of the locking member 52 relative to the internal shaft 40. This outward displacement causes the second plurality of teeth 66 to lockingly engage the first plurality of teeth (i.e. the locking mechanism). Additional clockwise rotation of knob 32, and therefore of internal shaft 40, effects a displacement of internal shaft 40 further into housing 38, and therefore closes the clamp arm 34 tighter against the support structure and pulls the support structure against the back of the medical instrument (i.e. the tightening mechanism). A stop member 72 fixed to the second cam member 46 rotates within the end plate 48 as the internal shaft 40 is rotated during the locking and tightening operations described above. A shoulder (not shown) fixed within the bore of the end plate cooperates with the stop member 72 to limit the rotational range of the second cam member 46, and thus the internal shaft 40, to prevent overtightening, which could damage the hanging apparatus 30.

Internal detents or stops associated with clamp shaft 36 may be included to allow the shaft/arm combination 36/34 to be easily positioned in either a horizontal or vertical orientation depending upon the specific application of the clamp. Likewise, appropriately positioned detents or stops in association with internal shaft 40 and cammed surfaces 46, 52, and 58 allow a definitive tightening of the clamp that prevents a reverse rotation of internal shaft 40 under the influence of the cammed surfaces. Retention spring 60 is positioned to ensure that the short rack cammed surface 52 is pulled down when the cam is rotated.

It should be apparent from the foregoing that an invention having significant advantages has been provided. While the invention is shown in only a few of its forms, it is not just limited but is susceptible to various changes and modifications without departing from the spirit thereof.

We claim:

1. A medical device hanging apparatus for facilitating the removable attachment of a medical instrument alternately to a vertical or a horizontal longitudinal support structure, the hanging apparatus comprising:
    a clamp shaft, the clamp shaft rotatable about a central longitudinal axis and comprising a cylindrical tube fixed with a clamp arm extending orthogonally from the clamp shaft;
    an internal shaft, the internal shaft comprising a longitudinal hollow structure positioned in telescoping fashion within the cylindrical tube of the clamp shaft;
    a clamp knob, the knob fixed to a first end of the internal shaft, as the internal shaft extends through the clamp shaft, in a manner that positions the clamp arm generally between the knob and the balance of the longitudinal clamp shaft;
    a tension spring, the spring positioned within and generally extending the length of the internal shaft, the spring fixed at a first end thereof to the first end of the internal shaft;
    a clamp housing, the housing comprising a longitudinal enclosure generally surrounding the clamp shaft and providing an aperture through which the clamp shaft extends, the clamp arm and the knob positioned external to the housing, a second end of the tension spring fixed to a point on the housing distal to the aperture such that telescoping withdrawal of the clamp shaft through the aperture is resisted by the tension spring, the clamp housing fixed in association with the medical instrument; and
    a rotational cam mechanism, the cam mechanism positioned between the clamp housing and the internal shaft wherein rotation of the internal shaft, as effected by rotation of the knob, directs a longitudinal movement of the internal shaft, the attached knob, and therefore the clamp arm, in a manner that tends to close the hanging apparatus.

2. The apparatus according to claim 1, wherein the cam mechanism further comprises:
    first and second cam members fixed to the internal shaft and having complementary inclined surfaces;
    a locking member rotatably positioned on the internal shaft between the complementary inclined surfaces of the first and second cam members, the locking member including a plurality of teeth.

3. The apparatus according to claim 1 further comprising:
    a first plurality of teeth fixed to the clamp housing and positioned along the longitudinal enclosure of the clamp housing;
    wherein the internal shaft includes a substantially flat surface;
    wherein the cam mechanism further comprises:
        first and second cam members fixed to the internal shaft and having complementary inclined surfaces; and
        a locking member rotatably positioned on the internal shaft between the complementary inclined surfaces of the first and second cam members and including a second plurality of teeth, the locking member being positioned on the substantially flat surface of the internal shaft when the internal shaft is in an unlocked position, the locking member being moved off of the substantially flat surface when the internal shaft is rotated into a locked position such that the second plurality of teeth lockingly engage the first plurality of teeth.

4. The apparatus according to claim 3, wherein subsequent rotation of the internal shaft after being placed in the locked position results in a longitudinal movement of the internal shaft as the locking member follows the inclined surfaces of the first and second cam members.

5. The apparatus according to claim 3, wherein the first plurality of teeth are disposed on a housing cover of the clamp housing.

6. A medical device hanging apparatus for facilitating the removable attachment of a medical instrument alternately to a vertical or a horizontal longitudinal support structure, the hanging apparatus comprising:
    a clamp housing defining a longitudinal enclosure along which are positioned a first plurality of teeth;
    a clamp shaft retractably positioned within the longitudinal enclosure, the clamp shaft being rotatable about a central longitudinal axis and comprising a cylindrical tube fixed with a clamp arm extending from the clamp shaft;

an internal shaft having a substantially flat surface rotatably positioned within the cylindrical tube of the clamp shaft;

first and second cam members fixed to the internal shaft and having complementary inclined surfaces; and a locking member rotatably positioned on the internal shaft between the complementary inclined surfaces of the first and second cam members and including a second plurality of teeth, the locking member being positioned on the substantially flat surface of the internal shaft when the internal shaft is in an unlocked position, the locking member being moved off of the substantially flat surface when the internal shaft is rotated into a locked position such that the second plurality of teeth lockingly engage the first plurality of teeth.

7. The apparatus according to claim 6, wherein subsequent rotation of the internal shaft after being placed in the locked position results in a longitudinal movement of the internal shaft relative to the clamp housing as the locking member follows the inclined surfaces of the first and second cam members.

* * * * *